United States Patent
Shin et al.

(10) Patent No.: US 12,398,404 B2
(45) Date of Patent: Aug. 26, 2025

(54) METHODS AND CONSTRUCTS FOR TRANSIENT PRODUCTION OF LENTIVIRAL VECTOR

(71) Applicant: LONZA WALKERSVILLE, INC., Walkersville, MD (US)

(72) Inventors: Young Shin, Walkersville, MD (US); Anandita Seth, Walkersville, MD (US)

(73) Assignee: LONZA WALKERSVILLE, INC., Walkersville, MD (US)

(*) Notice: Subject to any disclaimer, the term of this patent is extended or adjusted under 35 U.S.C. 154(b) by 513 days.

(21) Appl. No.: 17/757,041

(22) PCT Filed: Dec. 17, 2020

(86) PCT No.: PCT/US2020/065458
§ 371 (c)(1),
(2) Date: Jun. 8, 2022

(87) PCT Pub. No.: WO2021/127076
PCT Pub. Date: Jun. 24, 2021

(65) Prior Publication Data
US 2023/0026345 A1   Jan. 26, 2023

Related U.S. Application Data

(60) Provisional application No. 62/949,848, filed on Dec. 18, 2019.

(51) Int. Cl.
*C12N 15/86* (2006.01)
*A61K 35/76* (2015.01)
*C12N 5/073* (2010.01)

(52) U.S. Cl.
CPC .............. *C12N 15/86* (2013.01); *A61K 35/76* (2013.01); *C12N 5/0603* (2013.01); *C12N 2510/02* (2013.01); *C12N 2740/15041* (2013.01)

(58) Field of Classification Search
CPC ....... C12N 15/86; C12N 5/0603; A61K 35/76
See application file for complete search history.

(56) References Cited

FOREIGN PATENT DOCUMENTS

| | | |
|---|---|---|
| CN | 102851262 A | 1/2013 |
| EP | 3489353 A1 | 5/2019 |
| JP | 2019/122371 A | 7/2019 |
| WO | 2018187231 A2 | 10/2018 |
| WO | 2019058108 A1 | 3/2019 |

OTHER PUBLICATIONS

Dull et al., A third-generation lentivirus vector with a conditional packaging system, Journal of Virology, 1998, 72(11):8463-8471.
(Continued)

*Primary Examiner* — Mark L Shibuya
(74) *Attorney, Agent, or Firm* — MEDLER FERRO WOODHOUSE & MILLS PLLC

(57) ABSTRACT

The present disclosure relates to methods for producing lentiviral vectors using mammalian cells. Specifically, the methods utilize three plasmids, rather than four, to provide the required packaging elements and transfer vector to a cell, allowing for the production of a large number of lentiviral vectors in mammalian cells, including suspension-based cells. These methods allow for the production of lentiviral vectors that can be tailored to include a specific gene of interest.

20 Claims, 3 Drawing Sheets

(56) References Cited

OTHER PUBLICATIONS

Merten et al., Production of lentiviral vectors, Molecular Therapy-Methods & Clinical Development, 2016, 3:16017 (1-14).
Dissen et al., In vivo manipulation of gene expression in non-human primates using lentiviral vectors as delivery vehicles, Methods, 2009, 49(1): 70-77.
Graham et al., A new technique for the assay of infectivity of human adenovirus 5 DNA, Virology, 1973, 52(2):456-67.
Chu et al., SV40 DNA transfection of cells in suspension: analysis of efficiency of transcription and translation of T-antigen, Gene, 1981, 13(2):197-202.
Gustafsson, et al., Codon bias and heterologous protein expression, Trends Biotechnol, 2004, 22(7):346-53.
Gustafsson et al., Engineering genes for predictable protein expression, Protein Expr Purif, 2012, 83(1):37-46.

METHODS AND CONSTRUCTS FOR TRANSIENT PRODUCTION OF LENTIVIRAL VECTOR

FIELD OF THE INVENTION

The present disclosure relates to methods for producing lentiviral vectors using mammalian cells. Specifically, the methods utilize three plasmids, rather than four, to provide the required packaging elements and transfer vector to a cell, allowing for the production of a large number of lentiviral vectors in mammalian cells, including suspension-based cells. These methods allow for the production of lentiviral vectors that can be tailored to include a specific gene of interest.

BACKGROUND OF THE INVENTION

Lentiviral vectors are one of the most commonly used delivery methods in the field of gene and cell therapy. In the process of lentiviral vector production, the sequences required for production of the vector are divided into several different plasmids or expression cassettes to minimize the chance of yeilding a replication-competent lentiviruse (RCL). In general, 3rd generation lentivirus production systems utilize four separate plasmids or expresseion cassettees that express:
1) Lentiviral group specific antigen (GAG) gene and a lentiviral polymerase (POL) protein;
2) Envelope protein (usually Vesicular Somatitis Virus Glycoprotein (VSV-G));
3) HIV regulator of expression of virion proteins (REV) protein; and
4) A Transfer vector (TV) containing a gene of interest (GOI).

In the most common approach, the above four plasmids are transiently transfected into cells to produce lentiviral vectors, which is labor-intensive and costly. The optimization of the amount of DNA required for transfection of four separate plasmids is also time consuming and tedious. In addition, transient transfection of four plasmids requires large amounts of plasmid DNAs, which introduces the potential inadvertent production of replication-competent lentiviruses, raising safety concerns.

What are needed to overcome difficulties associated with transient transfection of four plasmids, are methods for producing scalable amounts of lentiviral vector using transfection of fewer than four plasmids including a plasmid encoding a gene of interest. The present invention fulfills these needs.

SUMMARY OF THE INVENTION

In some embodiments, provided herein is a method of producing a lentiviral vector, comprising: transfecting a mammalian cell with a first nucleic acid encoding a lentiviral regulator of expression of virion proteins (REV) gene under control of a first promoter and an envelope glycoprotein gene under control of a second promoter, a second nucleic acid encoding a gene of interest under control of a third promoter, and a third nucleic acid encoding a lentiviral group specific antigen (GAG) gene and a lentiviral polymerase (POL) gene under control of a fourth promoter; culturing the transfected mammalian cell; and isolating the lentiviral vector.

DETAILED DESCRIPTION OF THE INVENTION

The use of the word "a" or "an" when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the method/device being employed to determine the value. Typically the term is meant to encompass approximately or less than 1%, 2%, 3%, 4%, 5%, 6%, 7%, 8%, 9%, 10%, 11%, 12%, 13%, 14%, 15%, 16%, 17%, 18%, 19% or 20% variability depending on the situation.

The use of the term "or" in the claims is used to mean "and/or" unless explicitly indicated to refer only to alternatives or the alternatives are mutually exclusive, although the disclosure supports a definition that refers to only alternatives and "and/or."

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited, elements or method steps. It is contemplated that any embodiment discussed in this specification can be implemented with respect to any method, system, host cells, expression vectors, and/or composition of the invention. Furthermore, compositions, systems, cells, and/or nucleic acids of the invention can be used to achieve any of the methods as described herein.

As used herein, "nucleic acid," "nucleic acid molecule," or "oligonucleotide" means a polymeric compound comprising covalently linked nucleotides. The term "nucleic acid" includes polyribonucleic acid (RNA) and polydeoxyribonucleic acid (DNA), both of which may be single- or double-stranded. DNA includes, but is not limited to, complimentary DNA (cDNA), genomic DNA, plasmid or vector DNA, and synthetic DNA. RNA includes, but is not limited to, mRNA, tRNA, rRNA, snRNA, microRNA, miRNA, or MIRNA.

A "gene" as used herein refers to an assembly of nucleotides that encode a polypeptide, and includes cDNA and genomic DNA nucleic acid molecules. "Gene" also refers to a nucleic acid fragment that can act as a regulatory sequence preceding (5' non-coding sequences) and following (3' non-coding sequences) the coding sequence. In some embodiments, genes are integrated with multiple copies. In some embodiments, genes are integrated at predefined copy numbers.

Lentiviral Vectors and their Production

Figure 1B:
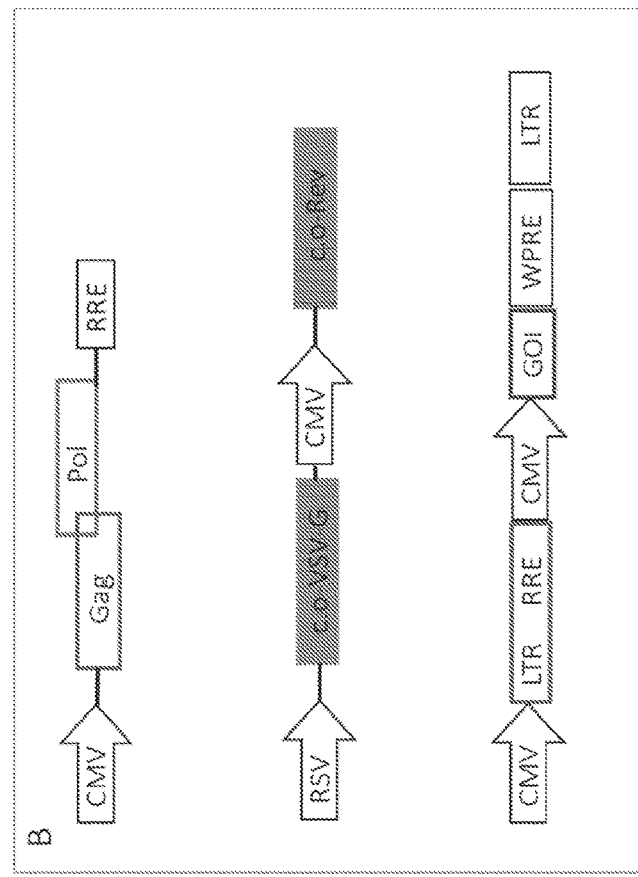
FIGS. 1A-1B are schematic representations of plasmids for lentivirus production in accordance with embodiments hereof.
Figure 1A:
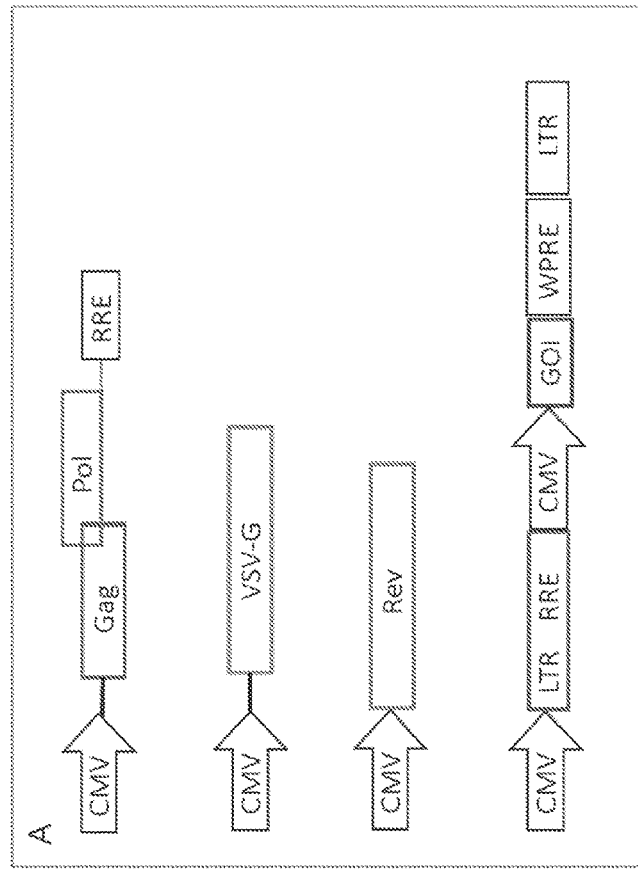

Lentiviral vector is a well studied vector system based on human immunodeficiency virus (HIV-1). Other lentiviral systems have also been developed as gene transfer systems, including HIV-2 simian immunodeficiency virus, nonprimate lentivruses, feline immunodeficiency virus, and bovine immunodeficiency virus, etc. Guided by safety concerns due to the pathogenic nature of HIV-1 in humans, the most widely used lentiviral system for use in clinical and research and development purposes is based on the four-plasmid system as shown in FIG. 1A, that expresses:

1) Lentiviral group specific antigen (GAG) gene and a lentiviral polymerase (POL) protein
2) Envelope protein (usually Vesicular Somatitis Virus Glycoprotein (VSV-G))
3) HIV regulator of expression of virion proteins (REV) protein; and
4) A Transfer vector (TV) containing a gene of interest (GOI).

Traditionally, mammalian cells, such as human embryonic kidney cells (e.g., HEK293) are transfected with each of the four plasmids as an adherent cell culture, and then the desired lentivirus containing the gene of interest is produced. Generally, these transiently transfected cells are able to produce lentivirus.

Lentiviral vectors are generally produced with a gene of interest that is to be introduced into a desired cell for therapy and disease treatment, including immunodeficiencies and neurodegenerative diseases.

The present invention provides improved methods of producing lentivirus, including methods for preparing lentivirus using a three plasmid system, including in cells that can be grown in suspension, allowing for a significant increase in the amount of lentivirus produced and a decrease in the amount of labor and time-intensive DNA amount optimization protocols.

In embodiments, provided herein is a method of producing a lentiviral vector, comprising transfecting a mammalian cell with a first nucleic acid encoding a lentiviral regulator of expression of virion proteins (REV) gene under control of a first promoter and an envelope glycoprotein gene under control of a second promoter, a second nucleic acid encoding a gene of interest under control of a third promoter, and a third nucleic acid encoding a lentiviral group specific antigen (GAG) gene and a lentiviral polymerase (POL) gene both under control of a fourth promoter.

Suitably, the cells that can be utilized in the various methods described herein are mammalian cells and cell lines or cultures. As used herein, the term "mammalian cell" includes cells from any member of the order Mammalia, such as, for example, human cells, mouse cells, rat cells, monkey cells, hamster cells, and the like. In some embodiments, the cell is a mouse cell, a human cell, a Chinese hamster ovary (CHO) cell, a CHOK1 cell, a CHO-DXB11 cell, a CHO-DG44 cell, a CHOK1SV cell including all variants (e.g. POTELLIGENT®, Lonza, Slough, UK), a CHOK1SV GS-KO (glutamine synthetase knockout) cell including all variants (e.g., XCEED™ Lonza, Slough, UK). Exemplary human cells include human embryonic kidney (HEK) cells, such as HEK293, a HeLa cell, or a HT1080 cell.

Mammalian cells include mammalian cell cultures which can be either adherent cultures or suspension cultures. Adherent cultures refer to cells that are grown on a substrate surface, for example a plastic plate, dish or other suitable cell culture growth platform, and may be anchorage dependent. Suspension cultures refer to cells that can be maintained in, for example, culture flasks or large suspension vats, which allows for a large surface area for gas and nutrient exchange. Suspension cell cultures often utilize a stirring or agitation mechanism to provide appropriate mixing. Media and conditions for maintaining cells in suspension are generally known in the art. An exemplary suspension cell culture includes human HEK293 clonal cells.

In embodiments, the methods described herein include producing a lentiviral vector. As used herein, a "vector" or "expression vector" is a replicon, such as a plasmid, phage, virus, or cosmid, to which a nucleic acid molecule described herein may be attached to bring about the replication and/or expression of the attached nucleic acid molecule in a cell. "Vector" includes episomal (e.g., plasmids) and non-episomal vectors. The term "vector" includes both viral and nonviral means for introducing a nucleic acid molecule into a cell in vitro, in vivo, or ex vivo. The term vector may include synthetic vectors. Vectors may be introduced into the desired host cells by well-known methods, including, but not limited to, transfection, transduction, cell fusion, and lipofection. Vectors can comprise various regulatory elements including promoters. A "lentiviral vector" refers to vector into which a desired gene can be inserted, suitably for use in a research or therapeutic application, for gene therapy purposes. Suitably, lentiviral vectors are from the HIV family.

"Transfection" as used herein means the introduction of an exogenous nucleic acid molecule, including a plasmid and/or vector, into a cell. A "transfected" cell comprises an exogenous nucleic acid molecule inside the cell and a "transformed" cell is one in which the exogenous nucleic acid molecule within the cell induces a phenotypic change in the cell. The transfected nucleic acid molecule can be integrated into the host cell's genomic DNA and/or can be maintained by the cell, temporarily or for a prolonged period of time, extra-chromosomally. Host cells or organisms that express exogenous nucleic acid molecules or fragments are referred to as "recombinant," "transformed," or "transgenic" organisms. A number of transfection techniques are generally known in the art. See, e.g., Graham et al., *Virology*, 52:456 (1973); Sambrook et al., Molecular Cloning, a laboratory manual, Cold Spring Harbor Laboratories, New York (1989); Davis et al., Basic Methods in Molecular Biology, Elsevier (1986); and Chu et al., Gene 13:197 (1981). Suitably, transfection of a mammalian cell with one or more of the vectors described herein utilizes a transfection agent, such as polyethylenimine (PEI) or other suitable agent, including various lipids and polymers, to integrate the nucleic acids into the host cell's genomic DNA.

Suitably, the nucleic acids with which the mammalian cells are transfected include lentiviral regulator of expression of virion proteins (REV) gene under control of a first promoter; an envelope glycoprotein gene under control of a second promoter; a gene of interest under control of a third promoter; and a lentiviral group specific antigen (GAG) gene and a lentiviral polymerase (POL) gene both under control of a fourth promoter. In embodiments, the gene or interest can be optionally utilized.

The lentiviral regulator of expression of virion proteins (REV) is an RNA-binding protein that promotes late phase gene expression. It is also important for the transport of the unspliced or singly-spliced mRNAs, which encode viral structural proteins, from the nucleus to the cytoplasm.

The envelope glycoprotein gene, suitably a Vesicular Somatitis Virus Glycoprotein (VSV-G) gene, is expressed and displayed on the surface of lentiviral vectors and mediates the transduction of lentiviral vector into the target cells.

GAG encodes a polyprotein that is translated from an unspliced mRNA which is then cleaved by the viral protease (PR) into the matrix protein, capsid, and nucleocapsid proteins. The lentiviral polymerase (POL) is expressed as a GAG-POL polyprotein as a result of ribosomal frameshifting during GAG mRNA translation, and encodes the reverse transcriptase, protease, and integrase. These three proteins are associated with the viral genome within the virion. Suitably the GAG gene is an HIV GAG gene and the POL gene is an HIV POL gene.

In suitable embodiments, nucleic acids including the nucleic acids encoding VSV-G and REV are codon-optimized. Additional elements used to produce the lentiviral vector can also be codon optimized.

As described herein, "codon optimization" is a process by which a nucleic acid sequence is processed via an algorithm to generate an "optimized" nucleic acid sequence that is statistically more likely to undergo successful translation by the ribosome of the host cell than any other nucleic acid sequence coding for the same protein. The process of codon optimization is made possible due to the inherent degeneracy of the genetic code, wherein multiple combinations of three base pairs can code for the same single amino acid.

Suitably, in the case of the nucleic acid encoding the GAG and Pol genes, the frame shift from GAG to Pol, as well as the polyprotein expression, is dependent on its native sequence. Thus, GAG and Pol are suitably excluded from codon-optimization to preserve their native sequences.

The methods for producing the lentiviral vector further comprise culturing the transfected mammalian cell to allow for production of the lentiviral vector, followed by isolating the mammalian cell to allow for further isolation of the lentiviral vector.

Methods for culturing the transfected mammalian cell are known in the art and include the use of various cell culture media, appropriate gas concentration/exchange and temperature control to promote growth of the cells and integration of the constructs into the genome of the cell.

Methods of isolating the viral vectors include various filtration techniques, including the use of sieves, filter apparatus, cell-selection apparatus and sorting, including magnetic sorting, cell counting, etc.

As noted herein, each of the components of the various nucleic acids (also called expression cassettes) are under the control of a promoter. As used herein "under control" refers to a gene being regulated by a "promoter," "promoter sequence," or "promoter region," which refers to a DNA regulatory region/sequence capable of binding RNA polymerase and initiating transcription of a downstream coding or non-coding gene sequence. In other words, the promoter and the gene are in operable combination or operably linked. As referred to herein, the terms "in operable combination", "in operable order" and "operably linked" refer to the linkage of nucleic acid sequences in such a manner that a promoter capable of directing the transcription of a given gene and/or the synthesis of a desired protein molecule is produced. The term also refers to the linkage of amino acid sequences in such a manner so that a functional protein is produced.

In suitable embodiments, the VSV-G gene expression is driven by a Rous sarcoma virus (RSV) promoter. An RSV long terminal repeat contains a transcriptionally potent enhancer and core promoter composed of a TATA box and an Inr-like sequence, termed the transcription start site core (TSSC) which is a strong promoter useful in a variety of cell types.

In embodiments, the REV gene expression is driven by a cytomegalovirus (CMV) promoter. It is an immediate-early enhancer and promoter of CMV suitably used for transient expression of transgenes in various cells.

In some examples of the present disclosure, the promoter sequence includes the transcription initiation site and extends upstream to include the minimum number of bases or elements necessary to initiate transcription at levels detectable above background. In some embodiments, the promoter sequence includes a transcription initiation site, as well as protein binding domains responsible for the binding of RNA polymerase. Eukaryotic promoters will often, but not always, contain "TATA" boxes and "CAT" boxes. Various promoters, including inducible promoters, may be used to drive the gene expression, e.g., in the host cell or vectors of the present disclosure. In some embodiments, the promoter is not a leaky promoter, i.e., the promoter is not constitutively expressing any of the gene products as described herein. In other embodiments as described herein, the promoter is a constitutive promoter, which initiates mRNA synthesis independent of the influence of an external regulation.

As described herein, suitably the mammalian cell is a mammalian cell culture, and in embodiments is a suspension culture. Exemplary cells include HEK293T cells.

In suitable embodiments, the gene of interest that is to be contained in the lentiviral vector is a gene of therapeutic interest. As referred to herein, the term "gene of interest" or "GOI" is used to describe a heterologous gene. As referred to herein, the term "heterologous gene" or "HG" as it relates to nucleic acid sequences such as a coding sequence or a control sequence, denotes a nucleic acid sequence, e.g. a gene, that is not normally joined together, and/or are not normally associated with a particular cell. In some embodiments, a heterologous gene is a construct where the coding sequence itself is not found in nature (e.g., synthetic sequences having codons different from the native gene). Allelic variation or naturally occurring mutational events do not give rise to heterologous DNA, as used herein.

As referred to herein, the term "gene of therapeutic interest" refers to any functionally relevant nucleotide sequence. Thus, the gene of therapeutic interest of the present disclosure can comprise any desired gene that encodes a protein that is defective or missing from a therapy-target cell genome or that encodes a non-native protein having a desired biological or therapeutic effect (e.g., an antiviral function), or the sequence can correspond to a molecule having an antisense or ribozyme function. Representative (non-limiting) examples of suitable genes of therapeutic interest include those used for the treatment of inflammatory diseases, autoimmune, chronic and infectious diseases, including such disorders as AIDS, cancer, neurological diseases, cardiovascular disease, hypercholestemia; various blood disorders including various anemias, thalassemias and hemophilia; genetic defects such as cystic fibrosis, Gaucher's Disease, adenosine deaminase (ADA) deficiency, emphysema, etc. Several antisense oligonucleotides (e.g., short oligonucleotides complementary to sequences around the translational initiation site (AUG codon) of an mRNA) that are useful in antisense therapy for cancer and for viral diseases have been described in the art and are also examples of suitable genes of therapeutic interest.

Production methods described herein can utilize any suitable reactor(s) including but not limited to stirred tank, airlift, fiber, microfiber, hollow fiber, ceramic matrix, fluidized bed, fixed bed, and/or spouted bed bioreactors. As used herein, "reactor" can include a fermenter or fermentation unit, or any other reaction vessel and the term "reactor" is used interchangeably with "fermenter." The term fermenter or fermentation refers to both microbial and mammalian cultures. For example, in some aspects, an example bioreactor unit can perform one or more, or all, of the following: feeding of nutrients and/or carbon sources, injection of suitable gas (e.g., oxygen), inlet and outlet flow of fermentation or cell culture medium, separation of gas and liquid phases, maintenance of temperature, maintenance of oxygen and $CO_2$ levels, maintenance of pH level, agitation (e.g., stirring), and/or cleaning/sterilizing. Example reactor units, such as a fermentation unit, may contain multiple reactors within the unit, for example the unit can have 1, 2, 3, 4, 5, 10, 15, 20, 25, 30, 35, 40, 45, 50, 60, 70, 80, 90, or 100, or more bioreactors in each unit and/or a facility may contain multiple units having a single or multiple reactors within the facility. In various embodiments, the bioreactor can be suitable for batch, semi fed-batch, fed-batch, perfusion, and/or a continuous fermentation processes. Any suitable reactor diameter can be used. In embodiments, the bioreactor can have a volume between about 100 mL and about 50,000 L. Non-limiting examples include a volume of 100 mL, 250 mL, 500 mL, 750 mL, 1 liter, 2 liters, 3 liters, 4 liters, 5 liters, 6 liters, 7 liters, 8 liters, 9 liters, 10 liters, 15 liters, 20 liters, 25 liters, 30 liters, 40 liters, 50 liters, 60 liters, 70 liters, 80 liters, 90 liters, 100 liters, 150 liters, 200 liters, 250 liters, 300 liters, 350 liters, 400 liters, 450 liters, 500 liters, 550 liters, 600 liters, 650 liters, 700 liters, 750 liters, 800 liters, 850 liters, 900 liters, 950 liters, 1000 liters, 1500 liters, 2000 liters, 2500 liters, 3000 liters, 3500 liters, 4000 liters, 4500 liters, 5000 liters, 6000 liters, 7000 liters, 8000 liters, 9000 liters, 10,000 liters, 15,000 liters, 20,000 liters, and/or 50,000 liters. Additionally, suitable reactors can be multi-use, single-use, disposable, or non-disposable and can be formed of any suitable material including metal alloys such as stainless steel (e.g., 316 L or any other suitable stainless steel) and Inconel, plastics, and/or glass.

Also provided herein are methods of treating a mammalian subject, suitably a human subject, with a lentiviral vector produced according to the various methods described herein. Suitably, the methods are used to treat a human subject with a gene of interested, including a gene of therapeutic interest. Administration to a human subject can include, for example, inhalation, injection, or intravenous administration, as well as other administration methods known in the art.

Exemplary mammalian cells are described herein, as are the gene components of the nucleic acids encoding the lentiviral packaging genes and gene of interest.

Methods of producing lentivirus are described herein, and suitably include inducing production of the products of the nucleic acids encoding the lentiviral packaging genes and the nucleic acid encoding the gene of interest, culturing the transfected mammalian cell, and harvesting the lentiviral vector.

ADDITIONAL EXEMPLARY EMBODIMENTS

Embodiment 1 is a method of producing a lentiviral vector, comprising: transfecting a mammalian cell with a first nucleic acid encoding a lentiviral regulator of expression of virion proteins (REV) gene under control of a first promoter and an envelope glycoprotein gene under control of a second promoter, a second nucleic acid encoding a gene of interest under control of a third promoter, and a third nucleic acid encoding a lentiviral group specific antigen (GAG) gene and a lentiviral polymerase (POL) gene both under control of a fourth promoter; culturing the transfected mammalian cell; and isolating the viral vector.

Embodiment 2 includes the method of embodiment 1, wherein the mammalian cell is a mammalian cell culture.

Embodiment 3 includes the method of embodiment 2, wherein the mammalian cell culture is a suspension culture.

Embodiment 4 includes the method of embodiment 1, wherein the mammalian cell is a HEK293T cell.

Embodiment 5 includes the method of any one of embodiments 1-4, wherein the envelope glycoprotein gene is a Vesicular Somatitis Virus Glycoprotein (VSV-G) gene.

Embodiment 6 includes the method of any one of embodiments 1-5, wherein the GAG gene is an HIV GAG gene and the POL gene is an HIV POL gene.

Embodiment 7 includes the method of any one of embodiments 5-6, wherein the nucleic acids encoding VSV-G and REV are codon-optimized.

Embodiment 8 includes the method of any one of embodiments 1-7, wherein the VSV-G expression is driven by a Rous sarcoma virus (RSV) promoter.

Embodiment 9 includes the method of any one of embodiments 1-8, wherein the REV gene expression is driven by a cytomegalovirus (CMV) promoter.

Embodiment 10 includes the method of any one of embodiments 1-9, wherein the gene of interest is a gene of therapeutic interest.

Embodiment 11 is a lentiviral vector produced by the method of any of embodiments 1-10.

Embodiment 11 is a method of treatment with a lentiviral vector, comprising: administering the lentiviral vector of claim 11 to a mammalian subject.

EXAMPLES

Example 1: Production of Lentiviral Vector Expressing GFP Using the 3-Plasmid System Materials and Methods Three plasmids (pUC-Gag-Pol, pUC-VSV-G-REV, and pUC-GFP) were constructed, the structure of which are represented in FIG. 1B. Shaded regions indicate the codon optimization of the VSV and Rev genes. These plasmids were transfected into a mammalian production cell line (HEK293 cells). After harvesting the viruses from these transfections, infectious lentiviral titers were measured using flow cytometry.

Results

Figure 2:
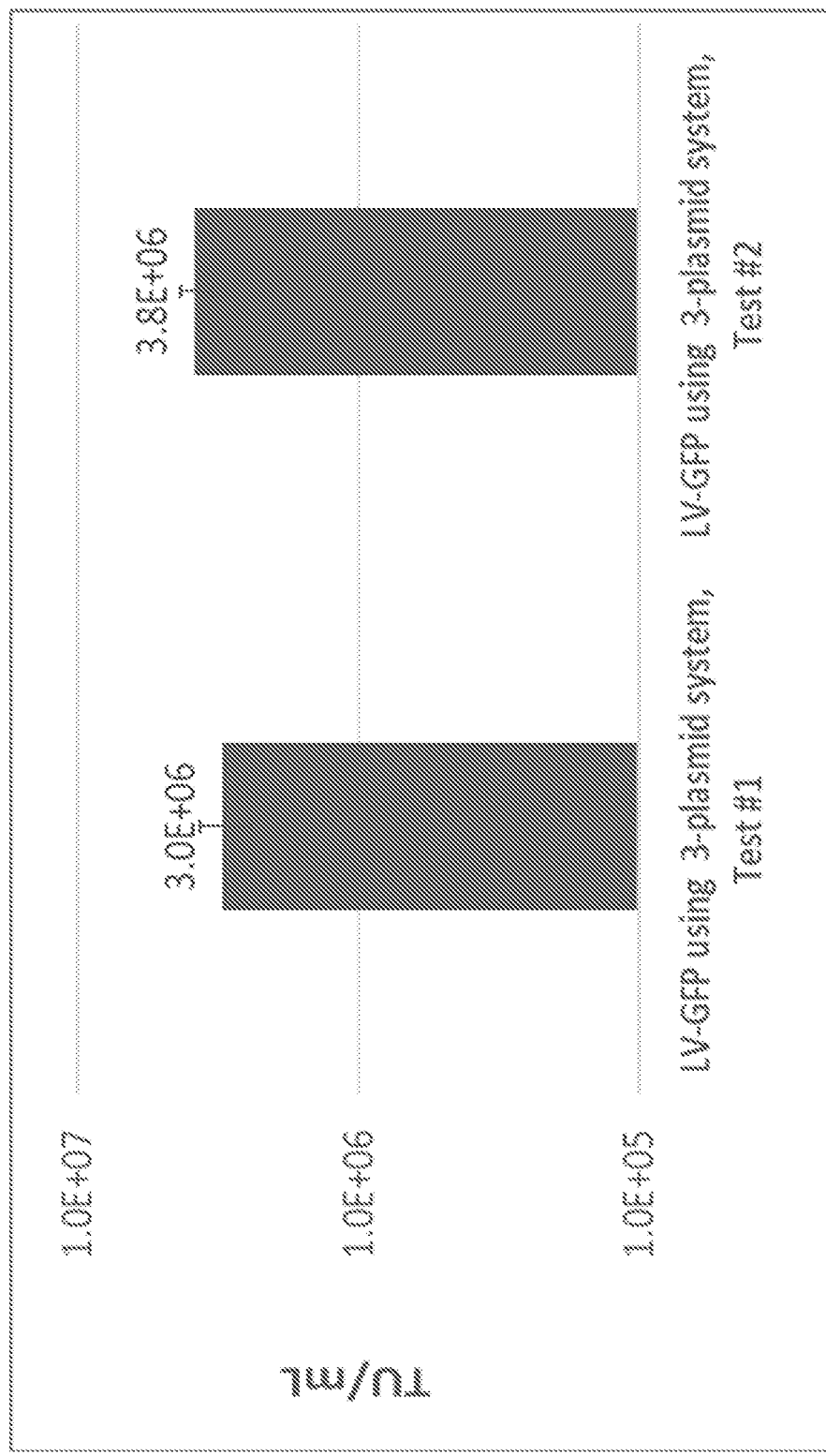
FIG. 2 shows the lentiviral titer achieved using the methods described herein (3-plasmid system) using GFP as the gene of interest.

As shown in FIG. 2, 3.0E+06 transduction units (TU) or more of LV-GFP were produced in one mililiter (mL) of cell culture harvest in test #1 and test #2, indicating that the 3-plasmid design is functional and produces lentiviral vectors via a triple plasmid transient transfection process.

Example 2: Production of Lentiviral Vector Expressing CD-19 CAR-T Using the 3-Plasmid System Compared to Commercially Available 4-Plasmid System Materials and Methods To confirm the efficacy of the 3-plasmid system in another context, an antibody sequence that has an affinity against CD-19 was employed as a GOI and cloned in the third plasmid transfer vector (hereafter, referred to as the "CD-19 CAR-T plasmid"). The CD-19 CAR-T plasmid was transfected plus pUC-Gag-Pol and pUC-VSV-G-REV into a mammalian cell line (HEK293 cells). For direct comparison of resulting lentiviral titers produced by 3- and 4-plasmid systems> The CD-19 CAR-T plasmid was transfected plus commercially available packaging plasmids from a 4-plasmid system into a mammalian cell line.

Results

Figure 3:
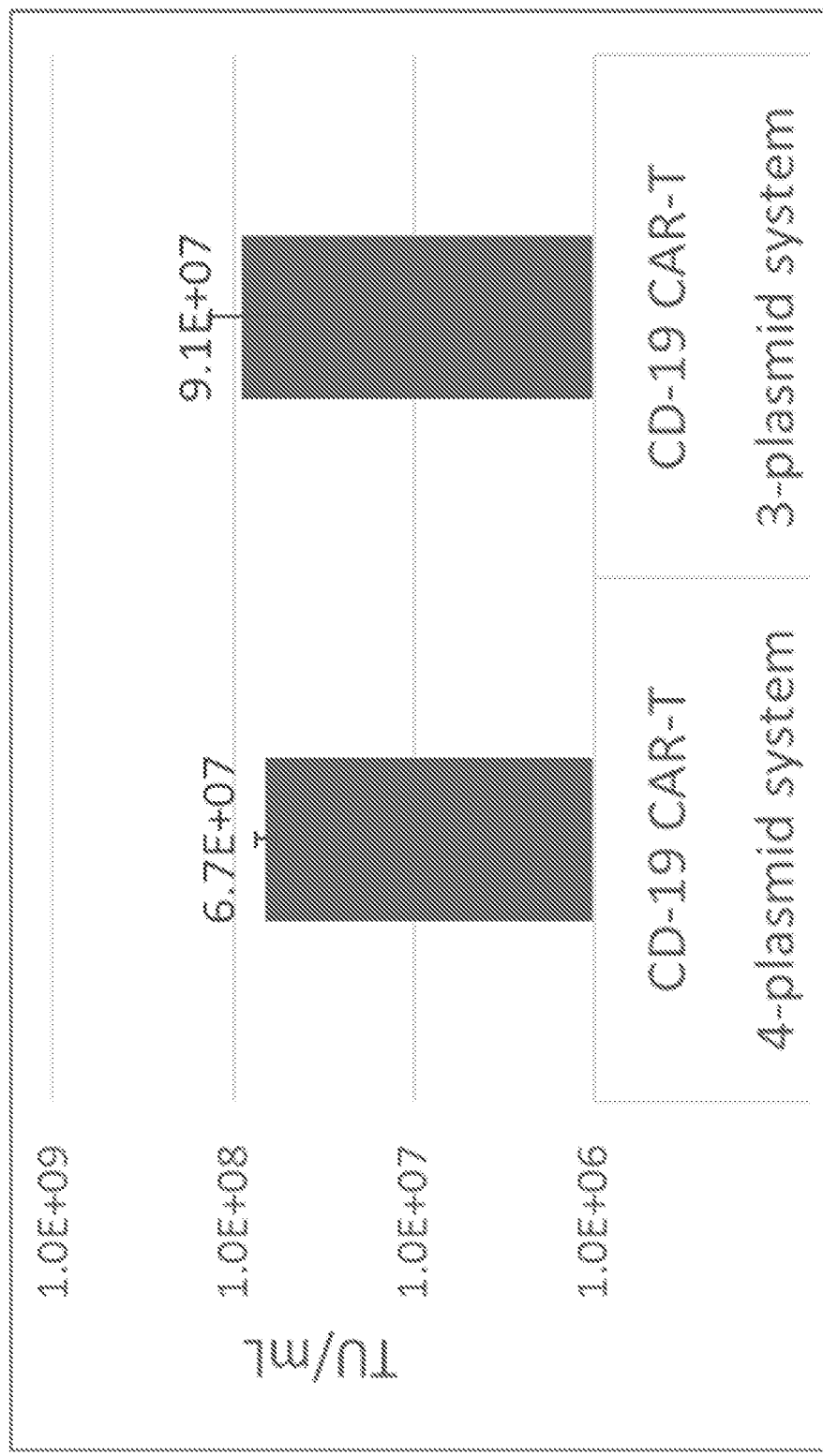
FIG. 3 shows the lentiviral titer achieved using the methods described herein (3-plasmid system) compared to commercially available products (4 plasmid system) using CD-19 CAR-T as the gene of interest.

The infectious lentiviral titers from each transfection were measured by droplet digital polymerase chain reaction (ddPCR). As shown in FIG. 3, LV-CD-19 CAR-T titer from the 3-plasmid system (9.1E+07 TU/mL) was comparable or suprior to the commercially available 4-plasmid system (6.7E+07 TU/mL). These results demonstrate that optimization of workflow using the 3-plasmid system to generate lentiviral vectors does not result in decreased transfection efficiency and production of viable transduction units compared to the commercially available 4-plasmid system.

It will be readily apparent to one of ordinary skill in the relevant arts that other suitable modifications and adaptations to the methods and applications described herein can be made without departing from the scope of any of the embodiments.

It is to be understood that while certain embodiments have been illustrated and described herein, the claims are not to be limited to the specific forms or arrangement of parts described and shown. In the specification, there have been disclosed illustrative embodiments and, although specific terms are employed, they are used in a generic and descriptive sense only and not for purposes of limitation. Modifications and variations of the embodiments are possible in light of the above teachings. It is therefore to be understood that the embodiments may be practiced otherwise than as specifically described.

All publications, patents and patent applications mentioned in this specification are herein incorporated by reference to the same extent as if each individual publication, patent or patent application was specifically and individually indicated to be incorporated by reference.

What is claimed is:

1. A method of producing a lentiviral vector, comprising:
   a. transfecting a mammalian cell with:
      i. a first nucleic acid molecule encoding a lentiviral regulator of expression of virion proteins (REV) gene under control of a first promoter and an envelope glycoprotein gene under control of a second promoter;
      ii. a second nucleic acid molecule encoding a gene of interest under control of a third promoter; and
      iii. a third nucleic acid molecule encoding a lentiviral group specific antigen (GAG) gene and a lentiviral polymerase (POL) gene both under control of a fourth promoter,
   wherein the first, second, and third nucleic acid molecules are three separate nucleic acid molecules;
   b. culturing the transfected mammalian cell; and
   c. isolating the lentiviral vector.

2. The method of claim 1, wherein the mammalian cell is a mammalian cell culture.

3. The method of claim 2, wherein the mammalian cell culture is a suspension culture.

4. The method of claim 1, wherein the mammalian cell is an HEK293T cell.

5. The method of claim 1, wherein the envelope glycoprotein gene is a Vesicular Somatitis Virus Glycoprotein (VSV-G) gene.

6. The method of claim 5, wherein the nucleic acids encoding VSV-G and REV are codon-optimized.

7. The method of claim 5, wherein the VSV-G gene expression is driven by a Rous sarcoma virus (RSV) promoter.

8. The method of claim 1, wherein the GAG gene is an HIV GAG gene and the POL gene is an HIV POL gene.

9. The method of claim 1, wherein the REV gene expression is driven by a cytomegalovirus (CMV) promoter.

10. The method of claim 1, wherein the gene of interest is a gene of therapeutic interest.

11. The method of claim 10, wherein the gene of therapeutic interest encodes for a protein.

12. The method of claim 10, wherein the gene of therapeutic interest encodes for an antibody.

13. The method of claim 10, wherein the gene of therapeutic interest encodes for a chimeric antigen receptor (CAR).

14. A lentiviral vector produced by the method of claim 1.

15. A method of treatment with a lentiviral vector, comprising:
   a. administering the lentiviral vector of claim 14 to a mammalian subject.

16. The method of claim 15, wherein the gene of interest encodes for a protein.

17. The method of claim 15, wherein the gene of interest encodes for an antibody.

18. The method of claim 15, wherein the gene of interest encodes for a CAR.

19. The lentiviral vector of claim 14, wherein the gene of interest encodes for a protein.

20. The lentiviral vector of claim 14, wherein the gene of interest encodes for a CAR.

* * * * *